(12) United States Patent
Luce

(10) Patent No.: US 7,004,902 B2
(45) Date of Patent: Feb. 28, 2006

(54) METHOD AND APPARATUS FOR MEASURING BIOMECHANICAL CHARACTERISTICS OF CORNEAL TISSUE

(75) Inventor: David A. Luce, Clarence, NY (US)

(73) Assignee: Reichert, Inc., Depew, NY (US)

( * ) Notice: Subject to any disclaimer, the term of this patent is extended or adjusted under 35 U.S.C. 154(b) by 348 days.

(21) Appl. No.: 10/394,833

(22) Filed: Mar. 21, 2003

(65) Prior Publication Data
US 2004/0183998 A1     Sep. 23, 2004

(51) Int. Cl.
*A61B 3/16* (2006.01)
(52) U.S. Cl. .................. 600/398; 600/405; 600/587
(58) Field of Classification Search ........ 600/398–406, 600/558, 561, 587
See application file for complete search history.

(56) References Cited

U.S. PATENT DOCUMENTS

| | | | |
|---|---|---|---|
| 5,474,066 A | 12/1995 | Grolman | |
| 6,113,542 A * | 9/2000 | Hyman et al. | 600/398 |
| 6,419,631 B1 | 7/2002 | Luce | |
| 6,817,981 B1 * | 11/2004 | Luce | 600/399 |

FOREIGN PATENT DOCUMENTS

EP          001147738 A1 * 10/2001

* cited by examiner

*Primary Examiner*—Charles Marmor
(74) *Attorney, Agent, or Firm*—Hodgson Russ LLP

(57) ABSTRACT

A method for measuring a biomechanical characteristic of corneal tissue of a cornea comprises the steps of measuring a geometric parameter of the cornea, measuring hysteresis associated with deformation of the cornea, and evaluating the measured geometric parameter and hysteresis. In an ophthalmic system for practicing the method, a pachometer is used to measure corneal thickness and a tonometer is used to measure hysteresis, and the measurement data is supplied to a computer for evaluation. A related method for prequalifying LASIK patients comprises the steps of establishing a multi-dimensional space wherein a first dimension is a geometric corneal parameter and a second dimension is hysteresis associated with corneal deformation, measuring the geometric corneal parameter and hysteresis of the patient's cornea, registering the geometric corneal parameter and corneal hysteresis in a data point in the multi-dimensional space, and evaluating a location of the data point in the multi-dimensional space.

27 Claims, 8 Drawing Sheets

FIG. 2A — CORNEA (CONVEX STATE)
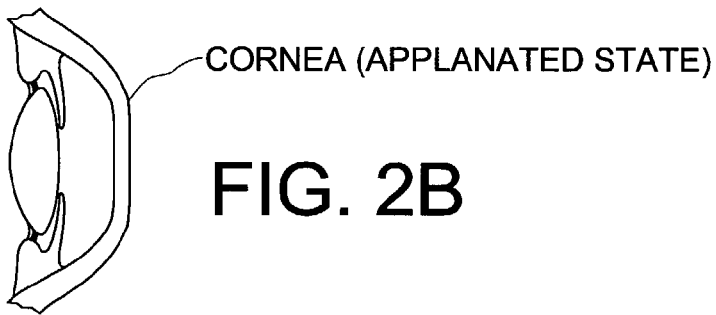
FIG. 2B — CORNEA (APPLANATED STATE)
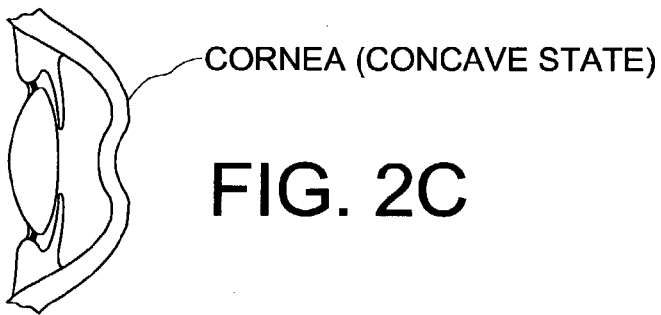
FIG. 2C — CORNEA (CONCAVE STATE)
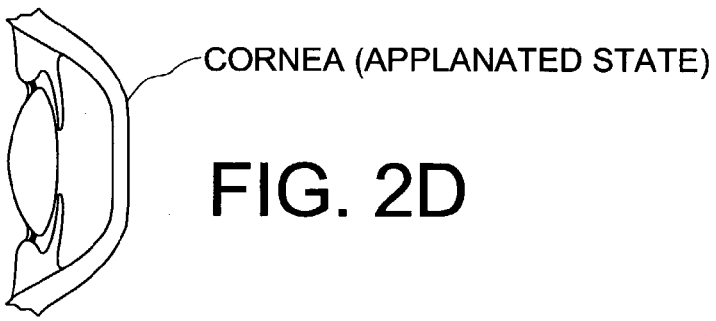
FIG. 2D — CORNEA (APPLANATED STATE)
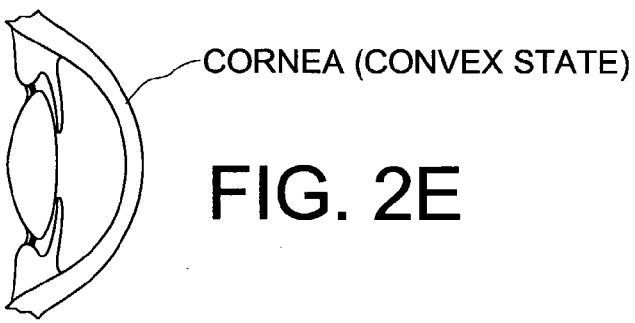
FIG. 2E — CORNEA (CONVEX STATE)

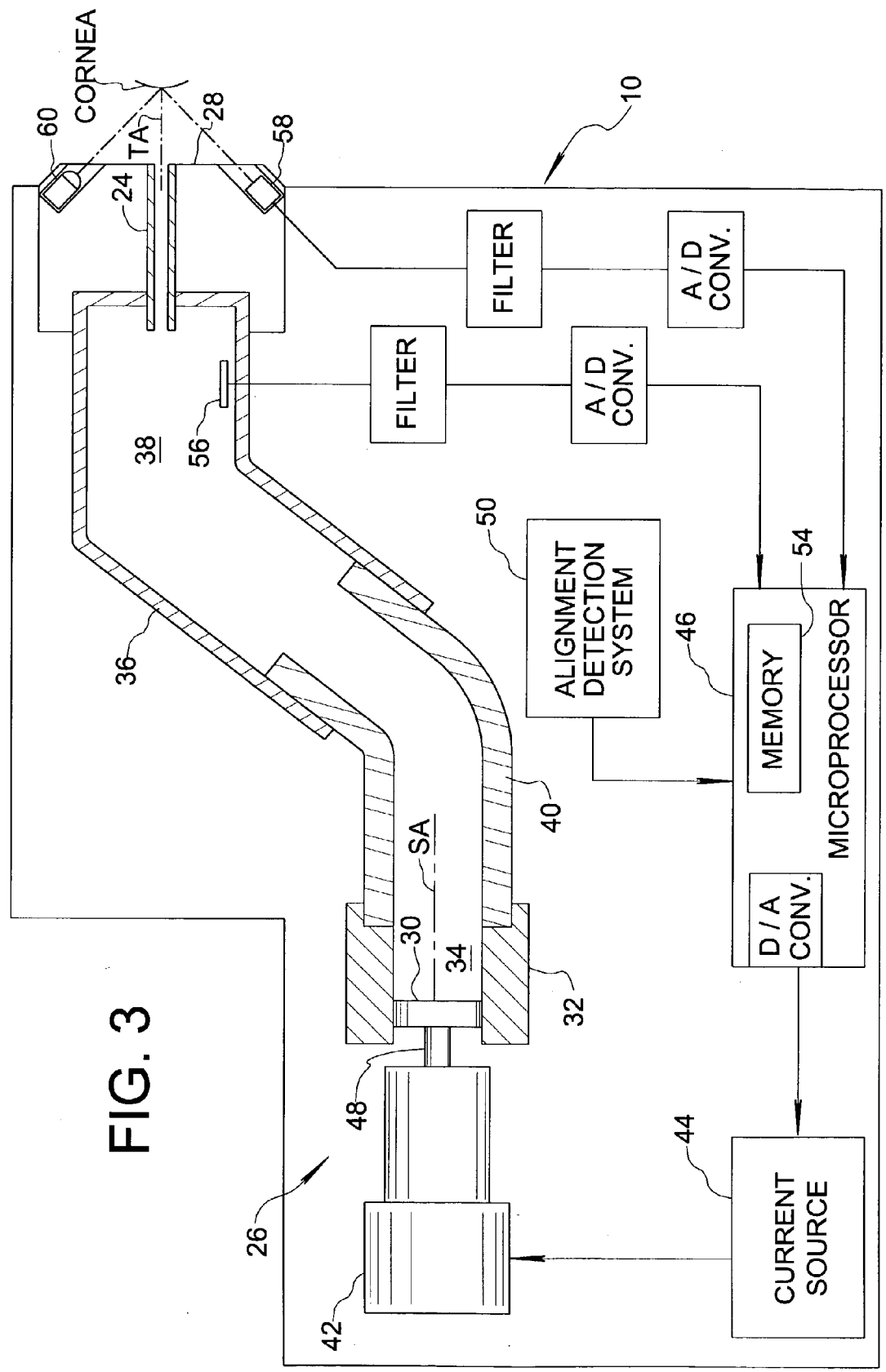

|F1| - |F2| => HYSTERESIS

METHOD AND APPARATUS FOR MEASURING BIOMECHANICAL CHARACTERISTICS OF CORNEAL TISSUE

FIELD OF THE INVENTION

The present invention relates generally to the field of ophthalmology, and more particularly to a method and apparatus useful for measuring intrinsic biomechanical properties of corneal tissue.

BACKGROUND OF THE INVENTION

LASIK (laser-assisted in situ keratomileusis) eye surgery has become a widely available treatment option for correcting refractive vision errors, primarily because it offers to reduce or eliminate a patient's current need for corrective lenses. In LASIK surgery, a special laser reshapes the cornea by removing corneal tissue in a controlled manner to change the cornea's refractive properties As LASIK surgery has grown in popularity, a condition known as progressive keratectasia has been identified as a rare but very serious complication in LASIK patients, and is characterized by a progressive steepening and thinning of the cornea followed by distortion, myopic shift and irregular astigmatism. It is thought that this condition is related to weakening of the cornea in cases where ablation surgery makes the cornea too thin. Consequently, it is widely believed that residual post-LASIK stromal thickness should not be less than 250 $\mu$m. As an alternative, some researchers suggest determining the acceptable residual stromal thickness by the initial corneal thickness (e.g., 55% of the initial corneal thickness), as this approach is purported to better reflect the individual nature of each cornea. It has also been proposed to reject surgery on corneas that are below a predetermined thickness, for example 500 $\mu$m. See, for example, *Journal of Cataract & Refractive Surgery*, Vo. 28, No. 12, December 2002, Editorial by Thomas Kohnen, MD. A shortcoming of these approaches to prequalifying patients is that they are based solely on corneal or stromal thickness, and do not take into account the intrinsic material properties or characteristics of the corneal tissue that, together with the corneal geometry, determine the cornea's ability to resist deformation. Therefore, a need exists for a method and system capable of measuring biomechanical characteristics of corneal tissue relating to elasticity and the ability to resist deformation.

SUMMARY OF THE INVENTION

The present invention provides a method and apparatus for measuring intrinsic biomechanical characteristics of corneal tissue. A potential application of the invention is prequalification of patients for LASIK surgery to reduce the occurrence of complications discussed above. A method of the present invention generally includes the steps of measuring a geometric parameter of a cornea, such as corneal thickness; measuring hysteresis associated with deformation of the cornea; and evaluating the measured geometric parameter and hysteresis. In a preferred method, evaluation is carried out by registering the measured geometric parameter and the measured hysteresis in a data point in multi-dimensional space, and evaluating a location of the data point in the multi-dimensional space.

The invention encompasses a related method of testing a patient's cornea to prequalify the patient for corneal ablation surgery comprising the steps of establishing a multi-dimensional space having a geometric corneal parameter dimension and a corneal hysteresis dimension; measuring the geometric corneal parameter and hysteresis of the patient's cornea; registering the measured geometric corneal parameter and measured hysteresis of the patient's cornea in a data point in the multi-dimensional space; and evaluating a location of the data point in the multi-dimensional space. In a disclosed prequalification procedure, the multidimensional space is divided into a plurality of different regions giving a general indication of the biomechanical characteristics of the tested corneal tissue so that a cornea having an unacceptably high risk of developing complications can be identified. For example, in a two-dimensional space having a corneal thickness dimension and a hysteresis dimension, the space could be divided into four quadrants: a first quadrant for thick corneas having a high hysteresis value, a second quadrant for thick corneas having a low hysteresis value, a third quadrant for thin corneas having a low hysteresis value, and a fourth quadrant for thin corneas having a high hysteresis value. The first quadrant represents a relatively low risk of future complications after LASIK surgery, while the third quadrant represents a relatively high risk. As another example, a qualification line, surface or other function can be established to divide the space into a higher risk region and a lower risk region.

An apparatus for carrying out the methods of the present invention comprises a pachometer for measuring corneal thickness, a tonometer for elastically deforming the cornea and measuring related hysteresis using detected pressures or forces associated with corneal applanation events, a computer receiving data from the pachometer and tonometer, and an output device connected to the computer. The pachometer and tonometer are preferably connected to the computer to provide measurement data directly to the computer, which is linked to the output device, which can be a display, printer, or other reporting device. The computer includes a memory for storing a normality function or other information for evaluating measurement data.

BRIEF DESCRIPTION OF THE DRAWINGS

The nature and mode of operation of the present invention will now be more fully described in the following detailed description of the invention taken with the accompanying drawing figures, in which:

FIGS. 2A–2E are a sequential series of views showing stages of deformation of a cornea by a tonometer during measurement of corneal hysteresis in accordance with a method of the present invention;

FIG. 3 is a schematic block diagram of a non-contact tonometer suitable for incorporation into an ophthalmic system as shown in FIG. 1;

DETAILED DESCRIPTION OF THE INVENTION

Figure 1:
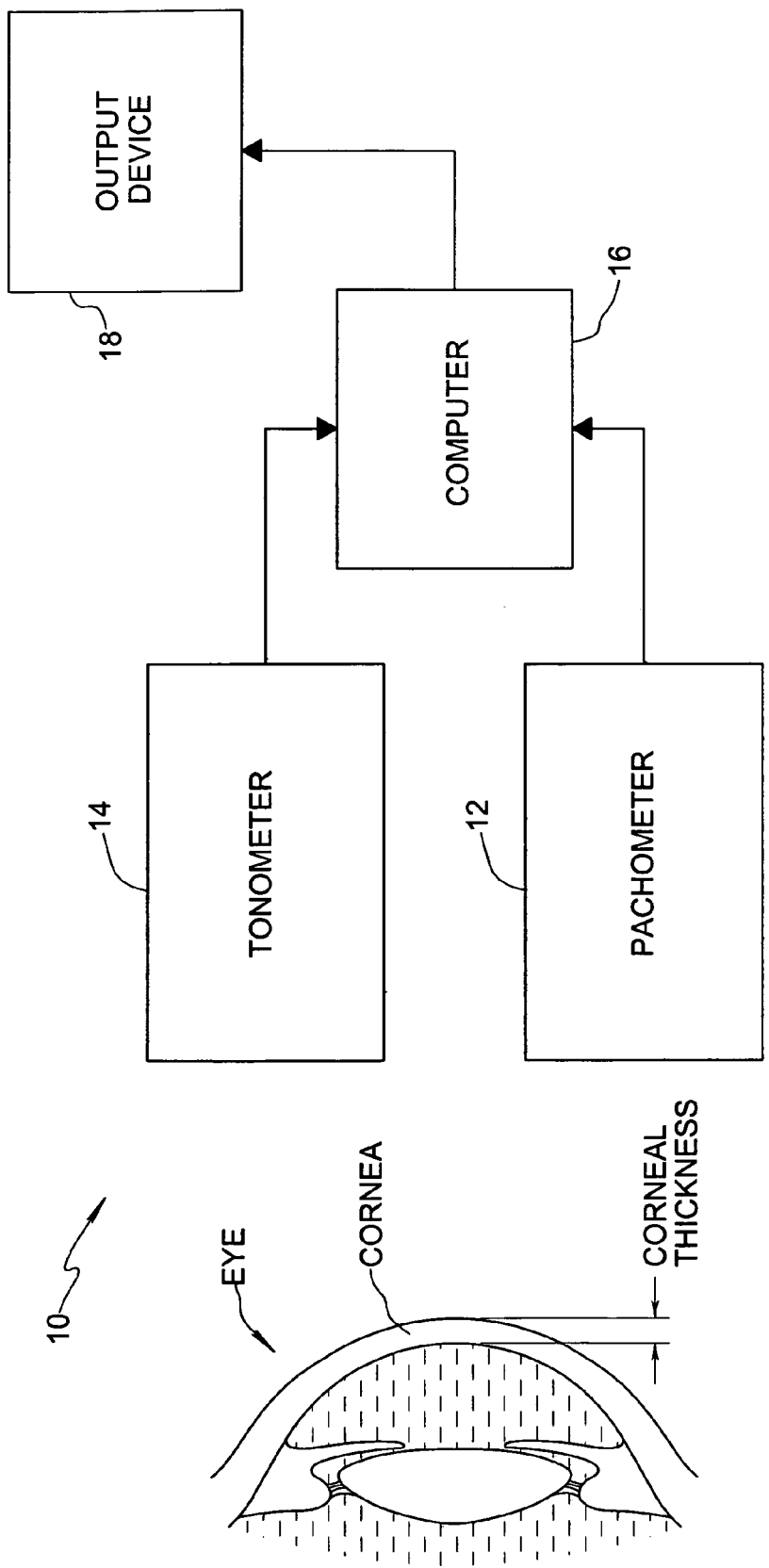
FIG. 1 is a schematic view of an ophthalmic system formed in accordance with the present invention.

Referring initially to FIG. 1 of the drawings, an ophthalmic system formed in accordance with the present invention is depicted schematically and identified by the reference numeral 10. Ophthalmic system 10 includes a pachometer 12 for measuring corneal thickness of an eye, a tonometer 14 traditionally used to measure intraocular pressure of an eye but now used to measure corneal hysteresis, a computer 16 connected to pachometer 12 and tonometer 14 to receive and evaluate measurement data from the pachometer and tonometer, and an output device 18 connected to the computer for reporting results.

Pachometer 12 can be any device capable of measuring corneal thickness, such devices being known in the field of ophthalmic instruments. In this regard, pachometer 12 can measure corneal thickness by an optical technique, an ultrasound technique, or by any other technique. Possible pachometers include, without limitation, slit lamp microscopes, specular microscopes, photo-pachometers, video-pachometers, and ultrasonic pachometers. Pachometer 12 provides corneal thickness measurement data to computer 16.

Tonometer 14 is used to determine corneal hysteresis associated with deformation of the cornea (tonometers are well-known in the ophthalmic art for measuring intraocular pressure, as opposed to corneal hysteresis). Tonometer 14 is preferably designed to deform the cornea from an initial convex state (FIG. 2A), through a first or inward state of applanation (FIG. 2B), to a concave state (FIG. 2C), and to allow the cornea to return from its concave state (FIG. 2C), through a second or outward state of applanation (FIG. 2D), to its original convex state (FIGS. 2E and 2A). A suitable tonometer 14 is shown schematically in FIG. 3 and is embodied as a non-contact tonometer operable to direct a fluid pulse at the cornea to cause the aforementioned deformation After a concave state (FIG. 2C) is reached, the fluid pulse dissipates and the cornea returns to its original convex state. Non-contact tonometer 14 includes alignment and tonometric measurement systems, and operates by discharging a fluid pulse through a fluid discharge tube 24 aligned along a test axis TA to cause observable deformation of a patient's cornea. The fluid pulse is generated by a fluid pump system 26 communicating with fluid discharge tube 24, which extends through a nosepiece 28. Fluid pump system 26 preferably comprises a piston 30 axially movable relative to a cylinder 32 along a stroke axis SA for compressing fluid within an internal compression chamber 34 defined thereby, a housing 36 defining an internal plenum chamber 38, and a flow tube 40 providing a fluid conduit from compression chamber 34 to plenum chamber 38. Fluid discharge tube 24 is mounted through the wall of housing 36 for guiding pressurized fluid from plenum chamber 38 along test axis TA directed at the patient's cornea.

A linear proportional solenoid 42 is operatively connected to piston 30 for causing axially directed movement of piston 30 relative to cylinder 32. A linear proportional solenoid is preferred because it is a specialized type of linear motor wherein the output driving force is proportional to the energizing current, and is most often used in connection with control valves. However, the drive means employed by fluid pump system 26 is not intended to be limited to this particular drive means, as other drive means such as rotary solenoids may possibly be used. Proportional solenoid 42 is connected to a current source 44 which supplies energizing current to the proportional solenoid under the control-of a microprocessor 46. A suitable linear proportional solenoid is a LEDEX® Linear Shift Solenoid Part No. 197887-001. As can be seen in FIG. 3, piston 30 is fixed for travel with a plunger 48 of proportional solenoid 42, as by threaded attachment or by fitted attachment with or without mechanical fasteners or adhesives.

Linear proportional solenoid 42 remains de-energized and piston 30 remains at rest until proper positioning of discharge tube 24 relative to the cornea is achieved as determined by an alignment detection system 50 connected to microprocessor 46. Alignment detection system 50 can be any suitable system, for example an alignment system as taught in commonly owned U.S. Pat. Nos. 4,881,807 and 6,361,495. Once alignment is achieved, microprocessor 46 provides a signal used by current source 44 to provide the driving current according to a preprogrammed ramp form, as will now be described below.

Figure 4:
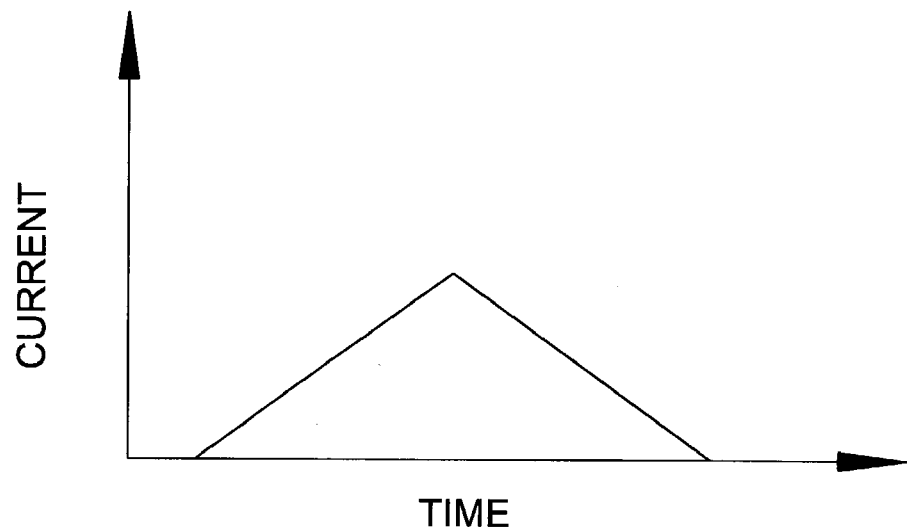
FIG. 4 is a graph of solenoid energizing current versus time during measurement of corneal hysteresis by the non-contact tonometer shown in FIG. 3.
Figure 5:
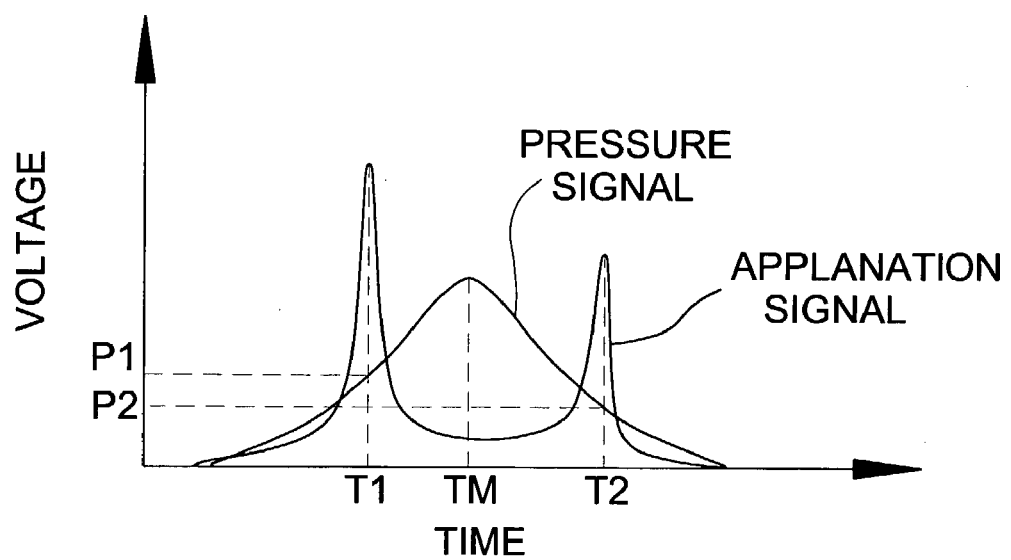
FIG. 5 is a graph showing time behavior of both an applanation signal and a pressure signal generated by the non-contact tonometer during measurement of corneal hysteresis.

A lookup table stored in a programmable memory 54 associated with microprocessor 46 includes digital information describing a predetermined current versus time relationship, which information is used to actually generate the energizing current supplied to proportional solenoid 42. The shape of the current ramp used to drive proportional solenoid 42 directly effects how the pressure within plenum chamber 38 changes as a function of time. A preferred current versus time profile is shown in FIG. 4. A pressure sensor 56, for example a pressure transducer or the like, is located within plenum chamber 38 for generating a pressure signal indicative of the fluid pressure within the plenum chamber. FIG. 5 includes a plot of a pressure signal corresponding to the current ramp shown in FIG. 4. In order to provide a signal indicative of the occurrence of applanation, a photosensitive detector 58 is positioned in a symmetrically oblique arrangement about test axis TA to receive corneally reflected light from emitter 60, whereby a peak signal is produced by detector 58 when the corneal surface is substantially flat for coherent reflection. FIG. 5 includes the applanation signal superimposed with the pressure signal, and the peaks in the applanation signal represent first and second applanation events corresponding to FIGS. 2B and 2D, respectively. As can be seen looking at FIGS. 4 and 5 collectively, the solenoid drive current increases linearly for a period of time longer than is necessary to achieve "inward" applanation represented by the first (left hand) peak in the applanation signal before it reverses slope and decreases at the same rate. FIG. 5 shows the resulting pressure-time curve, which is symmetrical about the instant the current reverses slope. As a result, the cornea is transfigured beyond the initial state of applanation to a state of concavity, and then returns through a second "outward" state of applanation to its original state of convexity as the plenum pressure decreases to atmosphere. The outward applanation is represented by the second (right hand) peak in the applanation signal shown in FIG. 5.

As will be observed from FIG. 5, the time T1 of inward applanation and the time T2 of outward applanation are not equidistant from a time TM when the pressure signal reaches a maximum, and the pressure P2 associated with the outward applanation event is less than the pressure P1 associated with the first applanation event. Applicant has experimentally confirmed that this observed hysteresis pressure differential is a rate dependent effect related to the velocity of the fluid pulse, and is not dependent upon intraocular pressure. More specifically, applicant has demonstrated that as the pressure ramp is slowed down, the hysteresis decreases in a corresponding manner. Thus, the hysteresis can be thought of as a manifestation of visco-elastic losses in the dynamic system that appear when the rate of the pressure ramp is sufficiently fast and are dependent on physical properties of the cornea, as opposed to intraocular pressure.

Corneal hysteresis (H) may be quantified directly as a difference between the signal amplitudes P1 and P2 from pressure sensor 56, namely:

$$H = P1 - P2;$$

or indirectly as a difference between tonometric measurements of intraocular pressure derived from P1 and P2. Intraocular pressures IOP1 and IOP2 corresponding to P1 and P2 are determined according to known procedure. More specifically, the analog signal information from pressure sensor 56 and photosensitive detector 58 for detecting applanation is filtered and converted to digital form for processing by microprocessor 46. The plenum pressures P1 and P2 at the times of applanation are then correlated by microprocessor 46 to respective IOP values (IOP1 and IOP2) in units of mmHg (millimeters mercury) using a regression equation developed and stored in instrument memory 54 during clinical calibration relative to GAT (Goldmann Applanation Tonometer) as a reference. Corneal hysteresis H is then quantified by finding the difference:

$$H = IOP1 - IOP2.$$

While the description above relates to an ophthalmic system wherein pachometer 12 and tonometer 14 are independent units connected to a common computer 16, the means for measuring corneal thickness and hysteresis could be integrated into a single instrument in accordance with the teaching of commonly owned U.S. Pat. No. 5,474,066.

Figure 6:
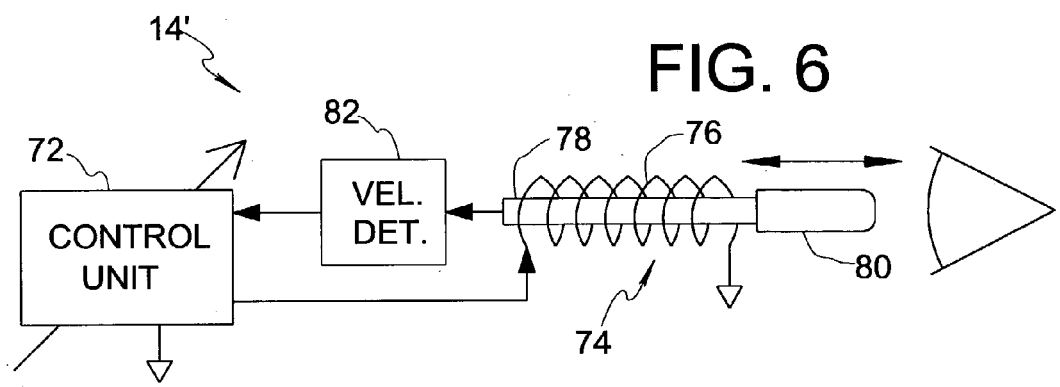
FIG. 6 is a schematic diagram of a contact type tonometer suitable for incorporation into an ophthalmic system as shown in FIG. 1.

It will be realized that corneal hysteresis can also be measured using a contact-type tonometer. For example, the pressure differential used to quantify hysteresis in the non-contact embodiment described above is analogous to a drive force differential associated with a contact tip of a contact tonometer. FIG. 6 shows a contact tonometer 14' in schematic representation as having an electronic control unit 72, a linear motor 74 having a coil 76 connected to the control unit 72 and a displaceable plunger 78, a rounded contact tip 80 fixed to a distal end of plunger 78, and a velocity detector 82 arranged to sense the velocity of plunger 78 and contact tip 80 and provide a corresponding output signal to control unit 72. Linear motor 74 is a constant force (versus position) linear proportional solenoid whose force is linearly proportional to the drive current supplied thereto, such as for example Ledex Part No. 197124-012.

Upon initiation of a signal to begin a measurement, such as by a manual trigger (not shown), the control unit 72 drives solenoid 74 "hard" until it reaches a predetermined velocity (PV). This creates a current spike at the beginning of the process before the contact tip 80 touches the eye. Upon reaching predetermined velocity PV, the solenoid current drops to zero (no force, constant velocity). At the instant contact tip 80 touches the eye, control unit 72 increases drive current, thereby increasing the force on contact tip 80, to maintain the predetermined velocity PV. The rounded shape of contact tip 80 causes the eye resistance force to increase due to the increasing area (as a function of eye depression). The visco-elastic resistance due to the corneal rigidity adds to the resistance due to IOP. The control unit detects the origin of the rising solenoid current and continues the constant velocity for a predetermined time (PT). Thus, the contact tip depresses the cornea a fixed distance (constant velocity multiplied by the predetermined time PT).

Figure 7:
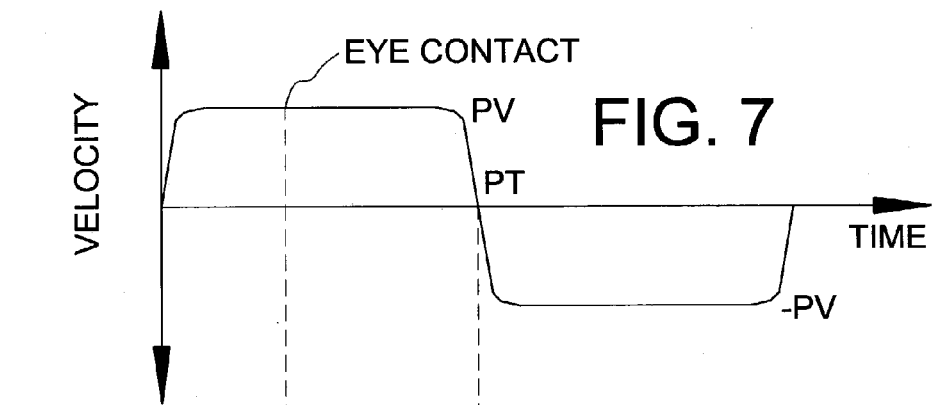
FIG. 7 is a plot of contact tip velocity versus time for a hysteresis measurement stroke performed using the contact tonometer of FIG. 6.
Figure 8:
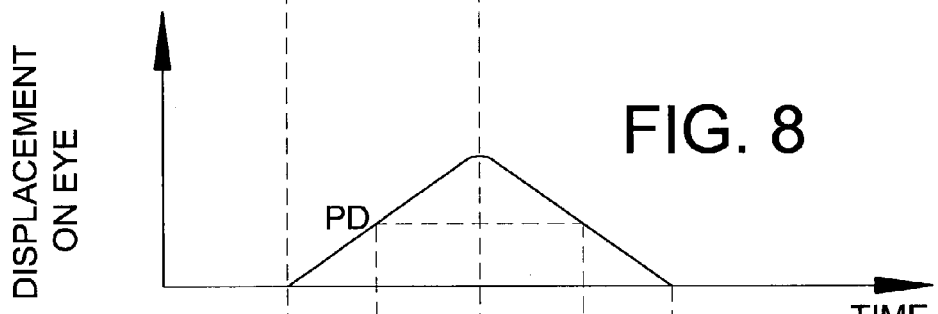
FIG. 8 is a plot of contact tip displacement on the eye versus time for the hysteresis measurement stroke of FIG. 7.
Figure 9:
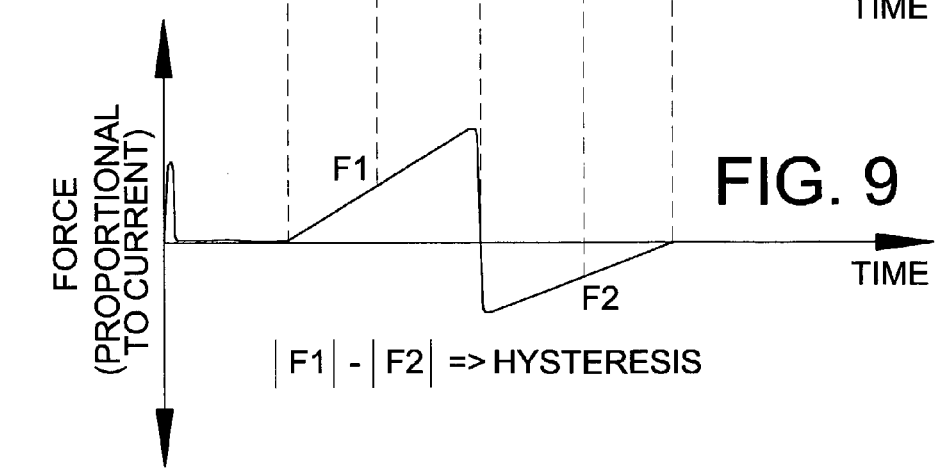
FIG. 9 is a plot of drive force on the contact tip versus time for the hysteresis measurement stroke of FIG. 7.

At the end of the predetermined time PT, the control unit sets a predetermined velocity −PV equal to the negative of the first predetermined velocity PV. The linear motor 74 reverses direction and contact tip 80 withdraws from the eye. In this case, the visco-elastic forces subtract from the IOP forces. The linear motor 74 is now balancing a reduced force from the eye and therefore has a lower current. Plots of the velocity, displacement, and solenoid force are shown in FIGS. 7–9, respectively. The magnitude of the force (current to the linear motor) at the time of a predetermined displacement (PD) on the eye is determined for both the inward and outward strokes. These forces are designated F1 and F2 in FIG. 9. The difference between these two forces serves as a measure of corneal hysteresis, and the measured IOP is proportional to the average of the two forces. Thus, contact tonometer 70 provides a measurement of corneal hysteresis in accordance with the present invention. The entire measurement takes place in about ten milliseconds, rapid enough to produce significant visco-elastic resistance forces.

The methodology of the present invention whereby a rate dependent hysteresis effect is observed to provide a second dimension measurement datum related to corneal effects has heretofore been described in the context of a single tonometric measurement stroke. However, in a broad sense, the methodology of the present invention can be applied in the context of a two or more different measurement strokes run at different rates to allow observation of the rate dependent hysteresis effect. For example, in non-contact tonometer 14 shown in FIG. 3, a fast measurement mode having a steep pressure ramp at a rate R1 and a slow measurement mode having a more gradual pressure ramp at a rate R2 could be used to successively measure the same eye to provide an indication of corneal hysteresis. This approach is expressed mathematically as set forth below, wherein the following variables are defined:

R1=Ramp rate for one measurement ($\mu$sec/mmHg)
R2=Different ramp rate for another measurement($\mu$sec/mmHg)
P1=Pressure value from measurement at rate R1 (mmHg)
P2=Pressure value from measurement at rate R2 (mmHg)
P0=True intraocular pressure (mmHg)
H=Corneal hysteresis at average of rates R1 and R2 (mmHg)
h1=Corneal hysteresis at rate R1 (mmHg)
h2=Corneal hysteresis at rate R2 (mmHg)
k=proportionality constant ((mmHg)$^2$/$\mu$sec); and by definition:

$$P1 = P0 + h1 \tag{1}$$

$$P2 = P0 + h2 \tag{2}$$

$$h1 = k*R1 \tag{3}$$

$$h2=k*R2 \quad (4)$$

$$H=(h1+h2)/2 \quad (5).$$

Subtracting equation (2) from equation (1), $$P1-P2=h1-h2=k*(R1-R2) \quad (6)$$

and solving for k $$k=(P1-P2)/(R1-R2) \quad (7).$$

Therefore $$h1=k*R1=R1*(P1-P2)/(R1-R2) \quad (8)$$

$$h2=k*R2=R2*(P1-P2)/(R1-R2) \quad (9);$$

and thus $$H=(R1+R2)*(P1-P2)/(2*(R1-R2)) \quad (10).$$

Consequently, a "multiple shot" measurement approach using different pressure ramp rates permits measurement of corneal hysteresis. Therefore, it should be realized that the terms "deformation" and "deforming" relate to transfiguration of the cornea from its natural shape once as well as more than once.

A multiple measurement approach is more time consuming and has much poorer resolution than the single measurement approach, but it is conceptually sound. One factor having a negative impact on measurement accuracy is that intraocular pressure is somewhat dependent on the point in the cardiac pulse cycle at which it is measured. A typical non-contact tonometer measurement occurs within a time frame on the order of about four to five milliseconds, whereas the normal period of a human heart pulse is on the order of about 1000 milliseconds. Therefore, in a single shot inward-outward measurement as described previously herein, there is little variation in IOP due to the status of blood flow in the eye between the inward and outward applanation events. However, in a multiple shot measurement scheme, the various measurements would occur at random points along the cardiac pulse cycle instead of at substantially the same point. Therefore, a multiple shot measurement process according to the present invention preferably includes a phase synchronization step whereby the measurements are made at substantially the same point in the cardiac pulse cycle. For example, tonometer 14 could be equipped with a synchronizer as taught in U.S. Pat. No. 3,572,100.

Figure 10:
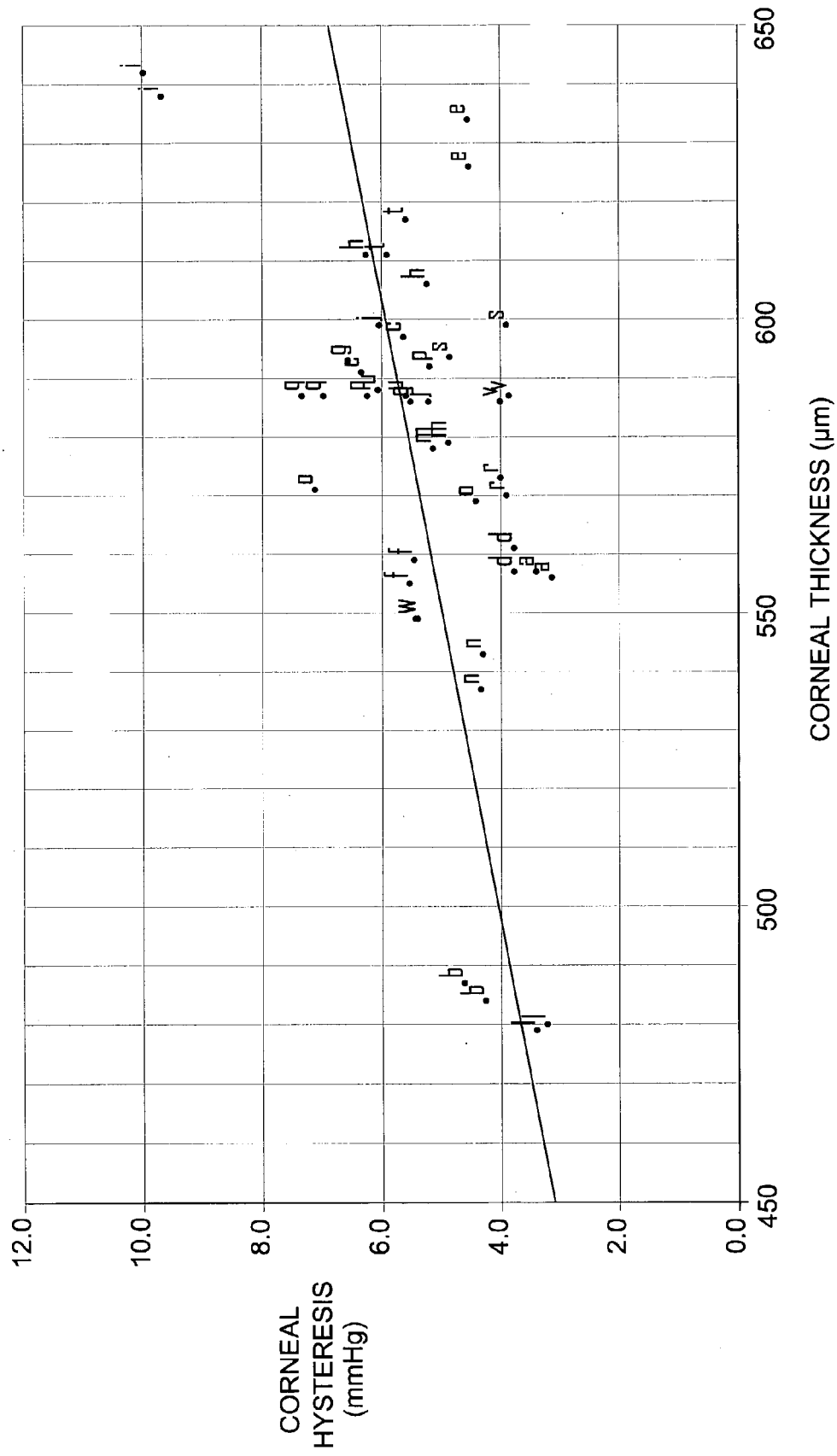
FIG. 10 is a plot of hysteresis versus corneal thickness including data from a plurality of tested eye pairs, wherein the plot includes a fitted line for the tested population of eyes.

The measured geometric information describing the cornea and the measured corneal hysteresis are evaluated to provide an indication of the intrinsic ability of the corneal tissue to resist deformation. FIG. 10 is a graph of hysteresis versus corneal thickness for a population of tested corneas. Lower case reference letters are used to identify left-eye and right-eye data points from the same individual. A normality line generated by least squares fit is shown. From a conceptual stand point, a tonometric measurement of intraocular pressure includes a first component attributed to the actual or true fluid pressure in the eye, and a second component attributed to corneal effects on the measurement. Notably, applicant has demonstrated experimentally that hysteresis is independent of the fluid pressure in the eye by testing the same eyes at both a normal pressure and an artificially elevated pressure. Thus, the hysteresis provides an indication of overall corneal effects on the tonometric measurement. The overall corneal effects are a function of both the corneal geometry and the intrinsic biomechanical characteristic of the corneal tissue material to resist deformation. For example, a thick cornea made of corneal tissue that has low resistance to deformation can exhibit hysteresis similar to that exhibited by a thin cornea made of corneal tissue that has a high resistance to deformation. Thus, the slope of the normality line of FIG. 10 is representative of intrinsic corneal tissue properties. It can be seen from FIG. 10 that most pairs of eyes have closely spaced data points, as would be expected. Eyes "e-e" exhibit corneal hysteresis that is lower than expected for such relatively thick corneas, while eyes "i-i" exhibit hysteresis that is greater than expected for corneas of similar thickness.

As mentioned in the Background of the Invention, qualifying a patient for corneal ablation surgery such as LASIK presently involves only an assessment of corneal geometry, and does not take into account the ability of the corneal tissue to resist deformation. However, certain corneas may be thick enough to qualify for surgery under present practice, but are formed of corneal tissue that exhibits poor resistance to deformation. Therefore, potentially serious post-surgical complications could nevertheless arise as described above. By contrast, certain corneas may be too thin to qualify for surgery under present practice, but are formed of corneal tissue that exhibits excellent resistance to deformation. Conceivably, such corneas might pose an acceptable risk for surgery. It will be appreciated that the method of present invention provides more information to a practitioner that can assist the practitioner in evaluating the risk of post-surgical complications.

Figure 11:
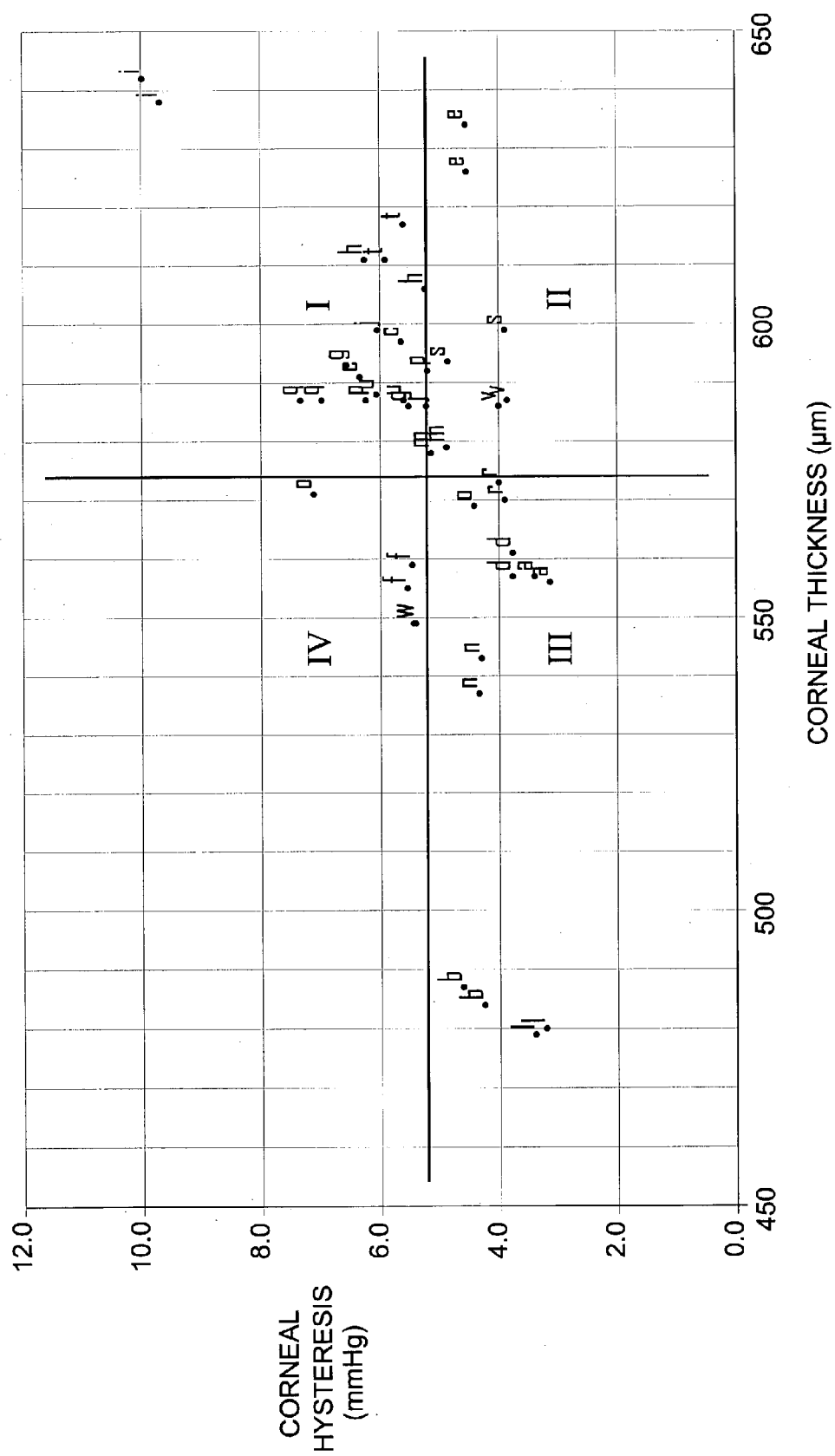
FIG. 11 is a plot similar to that of FIG. 10, wherein the two-dimensional space is divided into quadrants for patient prequalification purposes.
Figure 12:
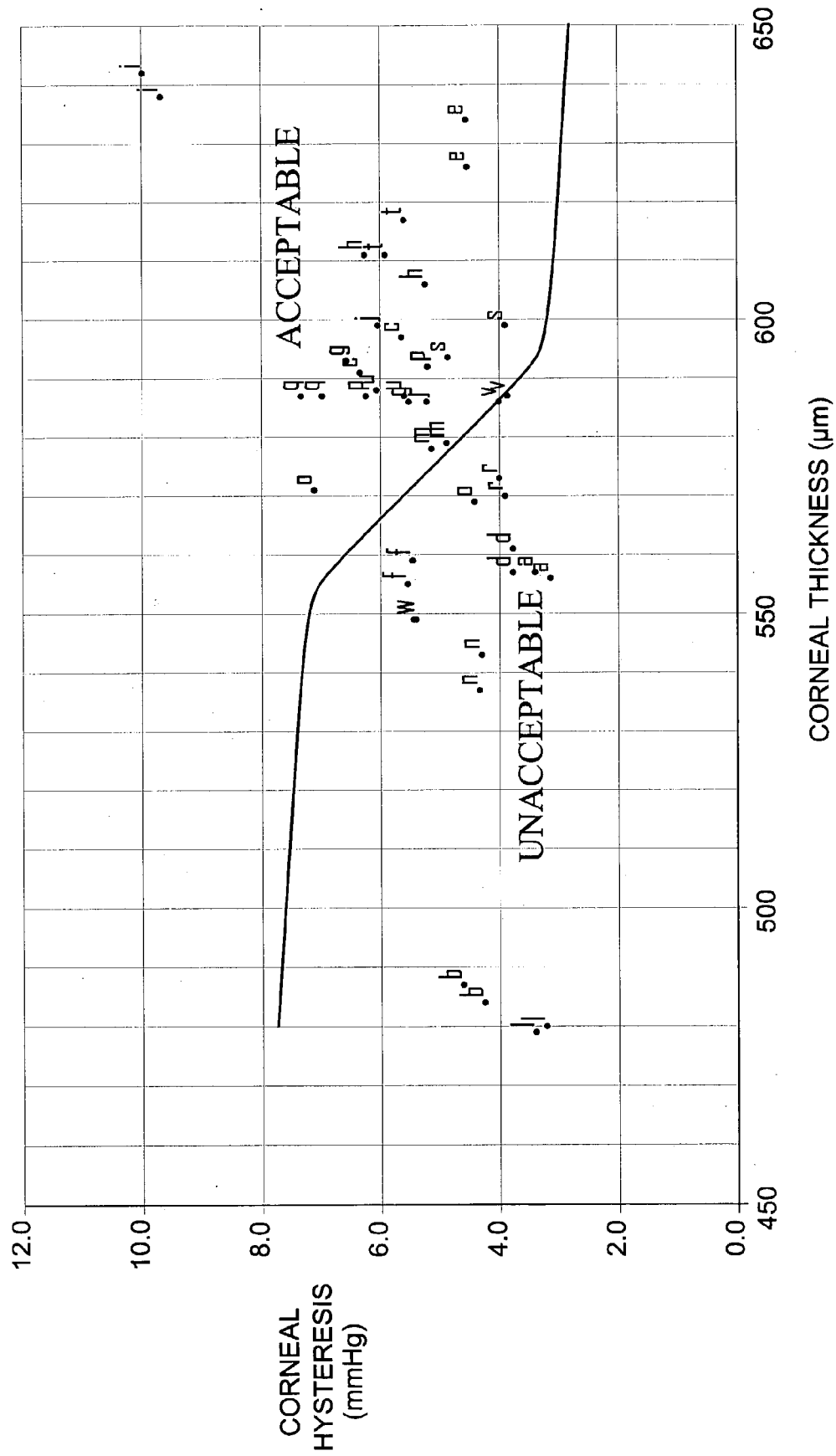
FIG. 12 is a plot similar to that of FIG. 10, wherein the two-dimensional space is divided into two regions for patient prequalification purposes.

FIGS. 11 and 12 illustrate possible schemes for prequalifying patients for corneal ablation surgery. In FIG. 11, the two-dimensional thickness-hysteresis space is divided by orthogonal lines into quadrants I, II, III, and IV. The orthogonal lines can, for example, intersect at an average corneal thickness and average hysteresis. Eyes are tested to measure thickness and hysteresis as described above, and the measurements are registered in a data point plotted in the thickness-hysteresis space. Data points located in quadrant I represent corneas that are thicker than average and show hysteresis that is higher than average, indicating these corneas are at relatively low risk of developing complications. Data points in quadrant III represent corneas that are thinner than average and exhibit lower than average hysteresis, indicating that these corneas are at a relatively high risk of developing complications. Data points in quadrant II represent corneas that are thicker than average but exhibit a lower than average hysteresis, indicating a level of risk somewhere between the levels associated with quadrants I and III. Similarly, data points in quadrant IV represent corneas that are thinner than average but exhibit a higher than average hysteresis, again indicating a level of risk somewhere between the levels associated with quadrants I and III. It is conceivable to use the normality line of FIG. 10 and a line perpendicular thereto as the axes of a quadrant division.

It is further conceivable to divide the thickness-hysteresis space into a plurality of regions based on collected data stored in a database that tracks post-surgical complications, so that a more realistic and evolving risk assessment scheme is possible. As a hypothetical example, FIG. 12 shows a qualification function that divides the thickness-hysteresis space into an acceptable risk region and an unacceptable risk region. Such a qualification function might be based on patient data collected over time, and could be adjusted as the database grows.

It is emphasized that the methodology of the present invention is not limited to using a two-dimensional space as shown, as further helpful information might be represented in another dimension. This being the case, the word "region" as used herein means an area, volume, or higher dimensional construct.

What is claimed is:

1. An ophthalmic system for measuring elasticity of corneal tissue forming a cornea, said system comprising:
   pachometer means for measuring thickness of said cornea;
   means for deforming said cornea;
   means for measuring hysteresis associated with deformation of said cornea; and
   a computer for receiving data generated by said pachometer means and said means for measuring hysteresis, and for evaluating said data to provide an indication of said elasticity.

2. The ophthalmic system according to claim 1, wherein said means for deforming said cornea and said means for measuring hysteresis are provided by a tonometer.

3. The ophthalmic system according to claim 2, wherein said tonometer is a non-contact tonometer.

4. The ophthalmic system according to claim 3, wherein said tonometer is a contact tonometer.

5. The ophthalmic system according to claim 1, wherein said computer includes a memory for storing population measurement data used to evaluate said data generated by said pachometer means and said means for measuring hysteresis.

6. A method for measuring a biomechanical characteristic of corneal tissue forming a cornea, said method comprising the steps of:
   measuring a geometric parameter of said cornea;
   measuring hysteresis associated with deformation of said cornea; and
   evaluating said measured geometric parameter and said measured hysteresis.

7. The method according to claim 6, wherein said geometric parameter is corneal thickness.

8. The method according to claim 6, wherein said step of measuring hysteresis comprises the following sub-steps:
   deforming said cornea, under increasing external pressure, from a natural convex state through a first applanated state and allowing said cornea to elastically return, under decreasing external pressure, through a second applanated state to said natural convex state;
   detecting a first pressure associated with said first applanated state and a second pressure associated with said second applanated state; and
   calculating said hysteresis using said first and second pressures.

9. The method according to claim 8, wherein said increasing external pressure and said decreasing external pressure are substantially symmetrical about a moment in time, and said hysteresis is proportional to a difference between said first and second pressures.

10. The method according to claim 8, wherein said step of deforming said cornea is performed using a tonometer.

11. The method according to claim 10, wherein said tonometer is a non-contact tonometer.

12. The method according to claim 10, wherein said tonometer is a contact tonometer.

13. The method according to claim 6, wherein said step of measuring hysteresis comprises the following sub-steps:
   (A) deforming said cornea, under increasing external pressure, from a natural convex state through an applanated state and allowing said cornea to elastically return, under decreasing external pressure, to said natural convex state, wherein said external pressure increases as a first function of time;
   (B) detecting a pressure associated with said applanated state;
   (C) repeating steps (A) and (B), but wherein said external pressure increases as a second function of time different from said first function of time; and
   (D) calculating said hysteresis using said pressures respectively associated with said applanated states.

14. The method according to claim 6, wherein said step of evaluating said measured geometric parameter and said measured hysteresis includes the following sub-steps:
   registering said measured geometric parameter and said measured hysteresis in a data point in multi-dimensional space; and
   evaluating a location of said data point in said multi-dimensional space.

15. The method according to claim 14, wherein said sub-step of evaluating a location of said data point includes comparing said location of said data point with an expected location of said data point.

16. The method according to claim 15, wherein said expected location of said data point is based on like data points from a population of corneas.

17. The method according to claim 14, wherein said multi-dimensional space is a two-dimensional space.

18. A method of testing a patient's cornea to prequalify said patient for corneal ablation surgery, said method comprising the steps of:
   establishing a multi-dimensional space wherein a first dimension is a geometric corneal parameter and a second dimension is hysteresis associated with corneal deformation;
   measuring said geometric corneal parameter and said hysteresis of said cornea;
   registering said geometric corneal parameter and said hysteresis of said cornea in a data point in said multi-dimensional space; and
   evaluating a location of said data point in said multi-dimensional space.

19. The method according to claim 18, wherein said geometric corneal parameter is corneal thickness.

20. The method according to claim 18, wherein said hysteresis of said cornea is measured using a tonometer.

21. The method according to claim 20, wherein said tonometer is a non-contact tonometer.

22. The method according to claim 20, wherein said tonometer is a contact tonometer.

23. The method according to claim 20, wherein said step of measuring hysteresis includes the following sub-steps:
   detecting, during a single elastic deformation of said cornea, a first pressure associated with a first applanated state of said cornea and a second pressure associated with a second applanated state of said cornea; and
   calculating a difference between said first and second pressures.

24. The method according to claim 20, wherein said step of measuring hysteresis includes the following sub-steps:
   deforming said cornea at a first rate and detecting a first pressure associated with an applanated state of said cornea;
   deforming said cornea at a second rate and detecting a second pressure associated with an applanated state of said cornea; and
   calculating said hysteresis using said first and second pressures.

25. The method according to claim 18, wherein said step of evaluating a location of said data point includes classifying said data point as falling within one of a plurality of predetermined regions in said multi-dimensional space.

26. The method according to claim 25, wherein said plurality of predetermined regions includes an acceptable region indicating the patient is acceptable for corneal ablation surgery.

27. The method according to claim 25, wherein said plurality of predetermined regions includes an unacceptable region indicating the patient is unacceptable for corneal ablation surgery.

* * * * *